(12) United States Patent
Koch et al.

(10) Patent No.: US 7,166,310 B2
(45) Date of Patent: Jan. 23, 2007

(54) **STABLE EXTRACT FROM *HYPERICUM PERFORATUM L.*, METHOD FOR THE PRODUCTION THEREOF AND ITS USE AS A TOPICAL MEDICAMENT**

(75) Inventors: Egon Koch, Karlsruhe (DE); Clemens Erdelmeier, Karlsruhe (DE); Joachim Herrmann, St. Leon-Rot (DE)

(73) Assignee: Dr. Willmar Schwabe GmbH & Co. (DE)

( * ) Notice: Subject to any disclaimer, the term of this patent is extended or adjusted under 35 U.S.C. 154(b) by 328 days.

(21) Appl. No.: 10/451,714

(22) PCT Filed: Dec. 21, 2001

(86) PCT No.: PCT/EP01/15281

§ 371 (c)(1),
(2), (4) Date: Feb. 23, 2004

(87) PCT Pub. No.: WO02/051427

PCT Pub. Date: Jul. 4, 2002

(65) Prior Publication Data

US 2004/0137088 A1    Jul. 15, 2004

(30) Foreign Application Priority Data

Dec. 22, 2000  (DE) .................. 100 64 284
Jun. 29, 2001  (DE) .................. 101 31 641

(51) Int. Cl.
*A61K 36/38* (2006.01)
*A61K 33/04* (2006.01)

(52) U.S. Cl. ....................... 424/730; 424/703
(58) Field of Classification Search ............... None
See application file for complete search history.

(56) References Cited

U.S. PATENT DOCUMENTS 6,063,401 A * 5/2000 Cody ................... 424/451
6,113,907 A * 9/2000 Khwaja et al. .......... 424/730
6,241,988 B1 * 6/2001 Erdelmeier et al. ...... 424/730
6,245,362 B1 * 6/2001 Elten et al. ............. 424/730
6,280,736 B1   8/2001 Erdelmeier et al.
6,291,533 B1 * 9/2001 Fleischner ............. 514/682
6,322,824 B1  11/2001 Chatterjee et al.

FOREIGN PATENT DOCUMENTS

| DE | 196 19 512 C1 | 7/1997 |
| DE | 199 03 570 | 5/2000 |
| DE | 198 54 446 | 6/2000 |
| DE | 198 54 446 A1 | 8/2000 |
| EP | 0 256 452 | 9/1991 |
| EP | 0 599 307 | 6/1994 |
| WO | WO 00/30660 | 6/2000 |

OTHER PUBLICATIONS

Erdelmeier, Studies in Natural Products Chemistry, (2000) 22:643-716.
Lavie, et al., Medicinal Research Reviewsi, (1995) 15(2):11-119.
Lavie, et al., Proc. Natl. Acad. Sci, USA, (1989) 86:5963-5967.
Maisenbacher, Tobingen University Dissertation, (1991) pp. 6-15.
Muller, et al., Deutsche Apotheker Zeitung, (1999) 139(17):49-58.
Schempp, et al., The Lancet, (1999) 353:2129.
Harald C. J. Orth and Peter C. Schmidt, "*Stability and Stabilization of Hyperforin*" Drugs made in Germany 42: pp. 110-113 (1999).

* cited by examiner

Primary Examiner—Christopher R. Tate
Assistant Examiner—Melenie McCormick
(74) Attorney, Agent, or Firm—McDonnell Boehnen Hulbert & Berghoff LLP

(57) ABSTRACT

The invention relates to an improved and stable (i.e. color-stable and, optionally, stable with regard to its hyperforin content) extract from the overground parts of *Hypericum perforatum L.*, to a method for the preparation thereof, and to pharmaceutical preparations and topical medicaments that contain this extract; in particular, gels for treating skin and mucous membrane irritations and disorders such as acne, atopic dermatitis, neuro-dermatitis, psoriasis, stomatitis, herpes zoster, herpes labialis (lip herpes), warts, varicella (chicken-pox), sores, burns and other bacterial and viral skin and mucous membrane infections and skin disorders that are accompanied by cell proliferation and inflammation.

24 Claims, No Drawings

STABLE EXTRACT FROM *HYPERICUM PERFORATUM L.*, METHOD FOR THE PRODUCTION THEREOF AND ITS USE AS A TOPICAL MEDICAMENT

This application is a National Stage of International Application No. PCT/EP01/15281, filed Dec. 21, 2001.

The present invention relates to an improved and stable (i.e. colour-stable and, optionally, stable with regard to its hyperforin content) extract from the exposed parts of *Hypericum perforatum L.*, to a method for the preparation thereof, and to pharmaceutical preparations and topical medicaments containing this extract, in particular, gels for treating skin and mucous membrane irritations and disorders such as acne, atopic dermatitis, neuro-dermatitis, psoriasis, stomatitis, herpes zoster, herpes labialis, warts, varicella (chicken-pox), sores, burns and other bacterial and viral skin and mucous membrane infections and skin disorders that are accompanied by cell proliferation and inflammation.

Hypericum extract has been used for the treatment of nervous disorders for many years past. Its application for depression and psycho-autonomic disorders has greatly increased over the past few years in the light of the favourable results of clinical trials [W. E. Müller, A. Singer, M. Wonnemann, DAZ 139 (17), 49–58 (1999)]. EP-A-O 599 307 describes a primary extract of St. John's wort. This primary extract was obtained by simple extraction of the drug with 96% or 60% aqueous ethanol. In DE-A-196 19 512, also DE-A-197 14 450, extracts are described that show a stable content of the otherwise highly unstable St. John's wort component hyperforin. WO 99/40905 describes the use of St. John's wort extract for the treatment and prophylaxis of dementia. Lastly, in DE-A-199 03 570, hyperforin preparations are described, in which hyperforin is present in the form of an extract of St. John's wort.

There is a venerable tradition of local application of hypericum extracts, particularly in the form of St. John's wort oil, for the treatment of sores, ulcers, burns, myalgia, bruises, etc [P. Maisenbacher, Tübingen University dissertation, 1991]. These empirical medical applications would appear to have a sound foundation in theoretical thinking and experimental investigations. There are many indications that hypericum extracts and individual ingredients make good use of anti-viral, anti-bacterial, anti-proliferative and inflammation-inhibiting properties.

Hypericin and pseudo-hypericin have been identified as the definitive ingredients with an anti-viral action in hypericum extracts [EP 0 256 452] [Lavie, G; Mazur, Y; Lavie, D; Meruelo, D: Med. Res. Rev. 15, (2), 111–119 (1995) [LAVIE, D; VALENTINE, F; LEVIN, B; MAZUR, Y; GALLO, G; LAVIE, D; WEINER, D; MERUELO, D. Proc. Natl. Acad. Sci. USA 86, (15) 5963–5967 (1989)]. These napthodianthrones also possess anti-viral properties against viruses (except retro-viruses) that are equipped with a lipid coating, for example the herpes virus. The anti-viral potency of hypericin is entirely contingent on photo-dynamic action, and is greatly intensified by the effect of visible light, a property that meant this ingredient was destined for local application on virus infections of the skin. Anti-viral effects have also been demonstrated for acetone and water extracts of hypericum, which contained predominantly catechols and flavone-aglyca [Erdelmeier, C; Koch, E; Hörr, R. *Hypericum perforatum L.*—St. John's wort, Chemical, Pharmacological and Clinical Aspects, in "Studies in Natural Product Chemistry" vol. 22, Atta-Ur-Rahman (editor), Elsevier Amsterdam, 2000). A therapeutically-relevant anti-viral effect might also be expected, especially when applied topically, in this ingredient. And in fact it has now been shown that extracts produced by this invention do indeed have anti-viral effects that are significantly greater than is the case with pure hypericin (see Example 3). At the same time, such extracts have a high therapeutic index, which hallmarks the difference between the desired anti-viral properties and non-specific cytotoxic effects.

Antibacterial effects of hypericum extracts are very well documented and can be attributed primarily to the hyperforin content. Hyperforin is particularly effective against gram-positive bacteria, and possesses antibacterial properties even, for example, in methicillin-resistant staphylococci, which represent major irritants in skin infections [Schempp, Ch. M; Pelz, K; Wittmer, A; Schoepf, E; Simon, J. C. Lancet 353 (9170), 2129—2129 (1999)]. This seems to be significant, since there is for example a close correlation between streptococci and staphylococci infections on the one hand and the induction, or recurrence, of psoriasis on the other. What we found surprisingly are the antibacterial effects of an extract according to the invention, which are significantly stronger than might have been expected on the basis of its hyperforin content. This means either that the extracts according to the invention contain other effective antibacterial ingredients, or that the effect of hyperforin is intensified by those components of the extract.

Besides its anti-viral effects, hypericin also has anti-proliferative properties and is therefore currently being clinically tested in tumours, in combination with photo-dynamic therapy. Suppression of cell proliferation is in all probability responsible for the inhibition of various protein kinases which play a part in intra-cellular signal transduction. Since this effect is also contingent on light, again the therapeutic use of this effect for topical application suggests itself. Here, we should be thinking primarily of the treatment of psoriasis, which is characterised by the hyper-proliferation of epidermal cells.

In addition, hyperforin possesses striking anti-phlogistic properties, whereby it suppresses for example the invasion of neutrophile granulocytes into inflamed tissue. The flavonoids contained in the hypericum extracts according to the invention also have inflammation-inhibiting effects. In particular, flavonoids have anti-oxidative properties, and are thus well placed to suppress the tissue-damaging effects of reactive oxygen radicals that are formed from leucocytes. It is known, moreover, that flavonoids can affect an array of enzyme systems that drive important cellular reactions which play a part in the pathogenesis of psoriasis, such as cell-proliferation and immune responses.

Psoriasis is a chronic skin ailment, hallmarked by hyper-proliferation and abnormal differentiation of keratinocytes, together with inflammation of the epidermis and dermis. While temporary alleviation of the symptoms and long-term containment of the condition is certainly possible using standard methods of treatment, a permanent cure of the condition is rarely achieved. All types of therapy hitherto in use have drawbacks that are serious to a greater or lesser degree (unpleasant smell, skin irritation, increased risk of skin cancer, teratogenicity, etc). Furthermore, there is an urgent need for effective methods for the treatment of psoriasis that produce few or no side-effects. Under our invention, this need is satisfied by the use of extracts of the overground parts of St. John's wort (*Hypericum perforatum L.*), which contain useful concentrations of hypericin, hyperforin and flavonoids.

One of the most prevalent skin ailments is acne. This is an inflammation of the sebaceous glands, which starts with the decay of sebaceous-gland follicles. Androgenous hormones are thought to trigger acne by stimulating the production of secretions in the sebaceous glands. If run-off disturbances arise simultaneously, this may lead to bacterial population of sebum, with subsequent peri-follicular inflammation, abscess formation, colliquation of the tissue and a foreign-body reaction. There are indications that the male hormone testosterone is converted into the biologically more potent form dihydro-testosterone in the skin of people suffering from acne when intensified under the effect of the enzyme 5α reductase. Inhibition of 5α reductase therefore presents a possibility for the treatment of acne. It was surprising to us that extracts according to the invention and various ingredients contained therein exert a marked inhibiting effect on this enzyme, and thus are therefore exceptionally well suited for the treatment of acne, given their antibacterial and inflammation-inhibiting properties.

The use of hyperforin, hypericin as dermatics, as well as extracts that contain those components, is already known from DE 198 54 446 A1 and WO 00/30660.

These total extracts are produced with a solvent mixture comprising ethanol with a high water content. According to the experience, these extracts contain high quantities of polyphenolic tannins (proanthocyanidines), which turn increasingly brown over time and ultimately make the preparation cosmetically unacceptable. This applies equally to the green pigments (chlorophylls) which pass from plant material in practically all ethanol-water-extracts. These pigments severely colour the extract and make them objectionable in appearance. Such extracts have been found completely unacceptable by patients. This applies in particular in the case of application to uncovered body areas.

The drawbacks just described can, according to the invention, be eliminated by using the colour-stable extract here described. Surprisingly, by an appropriate selection of extraction agent, the extraction of polyphenolic tannins can be suppressed. The green pigments present in the resulting primary extract can be largely removed by filtration via an adsorbing agent, for example an adsorbing resin. The extract finally obtained according to the invention is visually and cosmetically acceptable and can readily be incorporated into ointments, creams, gels, etc, for external use. The extract according to the invention is thus stable in the sense of being colour-stable; in other words, there is no unwanted change of color over the period when the medicament is being stored and used.

The absence, or at least substantial reduction, of any green pigments (chlorophylls) content and of polyphenolic tannins (proanthocyanidines) content can be demonstrated by the fact that absorption bands in the VIS spectrum of this extract, typical of chlorophyll, are greatly reduced between 600 and 700 nm or are absent altogether, and that no signal, or only a greatly-reduced signal, indicating the presence of proantho-cyanidines and chlorophyll, is visible in HPLC analysis.

The HPLC conditions for determining chlorophylls and proanthocyanidines are as follows:

Column: Spherisorb 100 RP-18/Merck (column length/diameter: 250/4 mm)

Eluant: A: $H_2O$ 100 parts/$H_3PO_4$ 0.3 parts/Triethylamine 0.2 parts

B: Acetonitril (ACN) 100 parts/$H_3PO_4$ 0.3 parts/Triethlyamine 0.2 parts

| Period | Eluant A | Eluant B | Flow, ml/min |
| --- | --- | --- | --- |
| 0.0 | 100 | 0 | 1.2 |
| 5.0 | 99 | 1 | 1.2 |
| 55.0 | 60 | 40 | 1.2 |
| 90.0 | 1 | 99 | 1.2 |
| 100.0 | 1 | 99 | 1.2 |
| 105.0 | 100 | 0 | 1.2 |

Flow: 1.2 ml/min
Analysis time: 100 min/gradient
Detection: UV 200–600 nm
Test quantity: 20 µl, approx 5 mg/ml
Column oven: 25° C.

Under the above HPLC conditions, chlorophylls appear at a detection wavelength of 400 nm with a retention-time in the 80 to 100 mins range.

Proanthocyanidines appear at a detection wavelength of 220 nm, as a broad peak with a retention-time in the range of 20 to 60 mins. The corresponding peaks for chlorophylls and proanthocyanidines appear at a 60% aqueous ethanol control extract, and are greatly reduced or are absent altogether in the extracts according to the invention.

Extraction agents deployed according to the invention are acetone, ethanol or a solvent mixture of acetone and ethanol. Preferred extraction agents are aqueous acetone, particularly ≧90% aqueous acetone, aqueous ethanol, especially ≧90% aqueous ethanol, or a mixture of both solvents, where a mixture of aqueous acetone and aqueous ethanol in the ratio of 8:2 is preferred, or a mixture of 95% by weight acetone and 92% by weight ethanol in the ratio of 8:2, is particularly preferred.

An adsorbing agent such as adsorbing resin can be deployed using the method according to the invention. Examples are resins based on polystyrol, such as the Diaion HP resins made by Mitsubishi Kasei Corporation. Another example of a suitable adsorbing agent is argillaceous earth, for example the Tonsil type, made by Südchemie plc.

The extracts of *Hypericum perforatum L.* according to the invention, with a reduced chlorophyll content and reduced proanthocyanidines content, should preferably have a hyperforin content of at least 2%, a total hypericin content of at least 0.2% and a total flavone content of at least 2%. Particularly preferred is a hyperforin content of at least 4%, a total hypericin content of at least 0.4% and a total flavone content of at least 4%, especially a hyperforin content of 4–8%, a total hypericin content of 0.4–1.0% and a total flavone content of 4–8%.

In the St. John's wort extract preparations according to the invention, we are concerned in particular with hydrophile or lipophile homogenous, single-phase preparations in gel form, for topical application (see examples 2a–2c). The gels are to be applied gently to the skin and rubbed in. In particular, they are cosmetically acceptable; in other words, there will be no unusual change of color of the skin when applied to uncovered parts of the body.

Examples of suitable excipients in normal pharmaceutical use for topical application, and suitable gel foundations in normal use, are polyacrylic acid, methyl cellulose and other cellulose derivatives.

Furthermore, the extract according to the invention has the advantage of containing the pharmacologically-relevant ingredients hyperforin, hypericins and flavones in ideal proportions. Given the complex pathogenesis of psoriasis, it would not be expected that substances with a single, selective mode of working could be successfully applied in the treatment of this ailment. This view is supported by clinical experience with established methods of therapy. The Hypericum extract according to the invention is thus exceptional in combining various modes of working that are vital in the treatment of psoriasis and other skin ailments (e.g. anti-viral, antibacterial, anti-phlogistic, anti-proliferative), such that it clearly surpasses the combined effect of the individual components on the working of individual substances (synergistic effect).

In order to stabilise the hyperforin in the extract or the pharmaceutical preparation, stabilisers can be added to the extract and/or the pharmaceutical preparation (e.g. gel) in an amount sufficient to stabilise hyperforin. As for the stabilisers themselves, we are talking about the stabilisers described in DE-A-196 19 512, which are preferably present at concentrations of 0.01% to 5%, especially 0.2% to 1%, in relation to the extract. In addition, with regard to the stabilisers, it may be a case of using the complexing agents described in DE-A-199 03 570 in sufficient amounts to complex the hyperforin. Explicit reference is made to both these references in connection with stabilising hyperforin.

EXAMPLE 1

Preparation of an Extract According to the Invention 3.1 kg of hypericum drug was homogenised for 1 min. with 6.5 times the quantity by weight of acetone 95%—EtOH 92% in the ratio of 8:2 as an extraction agent with ultraturrax (shielded from light). The solution was then extracted in the laboratory extractions vessel for 1 hour at 50° C. ($N_2$ atmosphere/shielded from light). 5 g ascorbic acid was added to the extract solution (1% to the expected quantity of extract). The solution was drawn through a vacuum filter (Seitz Supra 1500). The drug residue was again twice extracted and filtered with the 6-fold quantity by weight under the same conditions.

5 g ascorbic acid was once again added to the combined filtrates. The solution was gently concentrated until dry (heat-band max. 50° C./shielded from light).

Yield: 490.02 g=15.8% (hyperforin content: 5.75%/hypericin content 0.45%).

Next, the sample was dissolved in 92% by weight ethanol and filtered through a G2 frit. A negligible residue (approx. 2–3 g) was left on the frit. 485 g of extract was then passed to a closed chromatography column, packed with Diaion HP-20.

Chromatography Conditions:

| | |
|---|---|
| Sample | 485 g, diluted with 92% by weight EtOH to 15 l |
| Column size | Filling height 42 cm; radius 10 cm |
| Column filling | Diaion HP-20, 0.3–0.8 mm grain size |
| Eluant | 1. EtOH 92% by weight (100 l; → fraction 1) |
| | 2. EtOH 92% by weight (40 l; → fraction 2) |
| | 3. Acetone 100% (45 l; chlorophyll fraction) |
| Flow | Separation approx. 1 l/min. |

Yield:

Fraction 1 contained the main portion of the extract (412 g=85%; hyperforin content 6.3%; hypericin content 0.50%, total flavones 6.4%). This fraction was used in the invention examples as the St. John's wort extract according to the invention.

The extract showed no change of color at room temperature or at 30° C. over a period of 6 months.

EXAMPLE 2a

Hypericum Extract/Polyacrylate Gel

| Component | Quantity portion (%) |
|---|---|
| St. John's wort extract according to the invention, in accordance with Example 1 | 2.5 |
| Polyacrylic acid | 1.5 |
| Propylene glycol | 2.5 |
| Tromethamine solution (40%, in water) | 5.5 |
| Ethanol 96% by weight | 40.0 |
| Purified water | 48.0 |

Preparation:

The gel former (polyacrylic acid 1–3%, preferably 1.5%) was dispersed in a mixture of water, ethanol and propylene glycol. The extract (0.5–5%, preferably 2.5%) was added and blended in. The tromethamine solution was added and blended in small increments. A homogenous gel is formed. Stabilisers such as ascorbic acid can then be added to this basic recipe.

The preparation showed no change of color at room temperature or at 30° C. over a 6-month period.

EXAMPLE 2b

Hypericum Extract—Tenside Gel

| Component | Quantity portion (%) |
|---|---|
| St. John's wort extract according to the invention, in accordance with Example 1 | 5.0 |
| Macrogol-glycerol hydroxy-stearate | 35.0 |
| Isopropyl-myristate | 10.0 |
| Neutral oil | 10.0 |
| Propylene glycol | 5.0 |
| Purified water | 35.0 |

Preparation:

The St. John's wort extract, tenside (macrogol-glycerol-hydroxy-stearate), isopropyl-myristate, neutral oil and propylene glycol were blended until homogenous. Next, water was added while stirring. A homogenous gel is formed. Stabilisers such as ascorbic acid can be added to this basic recipe.

The preparation showed no change of color at room temperature or at 30° C. over a 6-month period.

EXAMPLE 2c

Hypericum Extract—Hydrocarbon Gel

| Component | Quantity portion (%) |
|---|---|
| St. John's wort extract according to the invention, in accordance with Example 1 | 5.0 |
| Vaseline | 90.0 |
| Propylene glycol | 5.0 |

Preparation:

The vaseline was melted by heating; propylene glycol was added and blended in. The St. John's wort extract was then added, blended in and stirred while cold. A homogenous gel is formed.

The preparation showed no change of color at room temperature or at 30° C. over a 6-month period.

EXAMPLE 3

Anti-Viral Effect

The Herpes simplex 1 strain of virus (HSV-1), (source: McIntyre, ATCC) was used to test the anti-viral properties of the extract in this invention.

Various concentrations of the test substances were blended with 980 µl of virus solution at a quantity of 20 µl to assess the cyto-toxic concentration ($TC_{50}$) and placed on a micro-titre dish with 3-day-old ape kidney cells (verocells) following a one-hour incubation period. After incubation of the dishes at 37° C. in an incubator for 5 days, a visual readout of the cell culture was performed, following HSV-1-specific cyto-pathogenic changes (CPE).

To determine "virostatic" action (inhibition test), the extract according to the invention or hypericin was added to a closed cohort of verocells in micro-titre dishes at various concentrations. After incubating for one hour, HSV-1 was then added at a concentration of 3000 $TCID_{50}$/ml. The dishes were then incubated at 37° C. and 5% $CO_2$ in the incubator. Assessment was carried out after 48–72 hours, using monoclonal antibodies and a specific colouring method.

Various concentrations of the extract according to the invention and hypericin were incubated in the incubator for 7 days to assess the cyto-toxic effect of verocells. Determining of cyto-toxicity was performed using an MTT test following a published procedure (Cinatl J. jr; Cinatl, J; Rabenau, H, Gümel, H; Doerr, H. W; (1993); "In-vitro anti-human immuno-deficiency virus activity of 2', 3 dideoxynucleotides and their effect on clonal growth of hæmopoietic cells from human bone-marrow", Arzneimittel-Frsch./Drug Res. 43, 622–625).

Assessment of the cyto-toxic concentration ($TC_{50}$) and the virus-inhibiting concentration ($IC_{50}$) was performed using linear regression. To calculate the therapeutic index, the formula $TC_{50}/IC_{50}$ was applied.

Results of the Investigations in the "Deactivation Test"

| Preparation | Concentrations applied in µg/ml | | | | |
|---|---|---|---|---|---|
| | 100 | 50 | 10 | 1 | 0.5 |
| St. John's wort extract according to the invention, in accordance with Example 1 | n.d. | n.d. | $3.6 \times 10^3$ | $8.4 \times 10^4$ | $8.4 \times 10^6$ |
| Hypericin | $4.7 \times 10^3$ | n.d. | $4.7 \times 10^6$ | n.d. | n.d |

The virus quantities applied were $1.5 \times 10^7$ $TCID_{50}$. "Virus deactivation" was calculated from the difference between the initial virus quantities and the virus titres given above. N.d. means "not determined", due to cyto-toxicity or the "virus-deactivating" effect found in preliminary trials.

Results of the Investigations in the "Inhibition Test"

| Preparation | $TC_{50}$ (µg/ml) | $IC_{50}$ (µg/ml) | Therapeutic index |
|---|---|---|---|
| St. John's wort extract according to the invention, in accordance with Example 1 | 1.3 | 0.012 | 108 |
| Hypericin | 74.3 | 2.2 | 34 |

As can be seen from the investigations, hypericin showed a clear virus-deactivating action, as expected. It amounted to approx. 4 log10 stages at 100 µg/ml. Surprisingly, however, the extract according to the invention produced a significantly more potent effect in that it showed an equally strong inhibiting effect even at a concentration of just 10 µg/ml, comparable to the more intrinsically anti-viral St. John's wort extract ingredient hypericin, which is contained in the extract according to the invention at a portion of 0.5% only.

The potent anti-viral effect of the extract according to the invention was confirmed in the inhibition test.

EXAMPLE 4

Antibacterial Effect

Anti-microbial effects against various gram-positive bacteria were determined using the micro-dilution method. In the table below, we show the minimum inhibition concentration (MIC) and the minimum bactericide concentration (MBC) in each case.

| Bacteria/fungi | Hyperforin MIC (µg/ml) | MIC of extract according to the invention (µg/ml) |
|---|---|---|
| Staphylococcus aureus (SA) | 62.5 | 39.0 |
| Staphylococcus saprophyticus | 62.5–125 | 19.5 |
| Methicillin-resistant SA | 31.25 | 9.8–19.5 |
| Enterococcus fæcalis | 125 | 39.0 |
| Enterococcus fæcium | 125–250 | 19.5 |
| Enterococcus durans | 125 | 9.8–19.5 |
| Listeria monocytogenes | 15.6–31.25 | 2.5 |
| Streptococcus pyogenes | 15.6 | 2.5–4.9 |

The extract according to the invention showed significantly more potent antibacterial effects on the gram-positive bacteria tested than would have been expected on the basis of its content of hyperforin, which is thought to be an ingredient with intrinsically antibacterial effects.

EXAMPLE 5

Anti-phlogistic Effect

The anti-phlogistic effects of hypericum extract according to the invention, also those of isolated ingredients, were tested in the Oleum Crotonis-ear-oedema model on male NRMI mice. After inducing a narcosis by the intra-peritonal injection of 60 mg/kg sodium-pento-barbital, the test substances were applied to the right ear in 10 µl acetone, whereas the left ear was treated with 10 µl acetone alone, as a control. 30 mins later, a local inflammation was triggered at the left ear by applying 50 µg Oleum Crotonis in 10 µl acetone. After 6 hours, the animals were sacrificed and inhibition of the inflammation reaction was quantified by weighing a sample of tissue drawn from both ears, using the following formula: $[1-(G_T/G_L] \times 100$; in the case of $G_T$ or $G_L$, this deals with the difference in weight between the right and left ears of animals that have been treated with the test substance ($G_T$), or only with the solvent ($G_L$).

Inhibition of neutrophile granulocyte accumulations in inflamed tissue was obtained by determining myelo-peroxidase (MPO) in the ear homogenates. To this end, biopsy samples were recorded in 1 ml hexadecyl-trimethyl ammonium bromide (HTAB) buffers, homogenised with a glass homogeniser at 4° C. and then given ultrasound treatment for 10 seconds in a sonicator. After centrifuging at 4° C. with 3000 g for 10 mins, the supernatant was removed and retained for analysing at −70° C. Determining the MPO was performed in micro-titre dishes after adding $H_2O_2$ and the O-dianisidine-dihydrochloride indicator as a kinetic measure, over a period of 5 mins at 450 nm. Assessment was carried out against a standard curve with horseradish peroxidase, and was obtained as an mU enzyme activity per mg of tissue.

The results of the investigations after applying 250 μg of the test substance or 1000 μg of the extract according to the invention to the left ear in each case are summarised in the following table.

| Ingredient | Oedema inhibition (%) | MPO inhibition (%) |
|---|---|---|
| Extract according to the invention | 69 | 72 |
| Amento-flavone | 82 | 70 |
| Biapigenine | 83 | 86 |
| Catechol | 36 | 41 |
| Chlorogenic acid | 14 | 16 |
| Epicatechol | 1 | 45 |
| Hyperforin | 65 | 62 |
| Hypericin | 6 | 48 |
| Hyperoside | −27 | 39 |
| Isoquercitrin | −29 | 73 |
| Camphor oil | 91 | 96 |
| Luteolin | 70 | 91 |
| Myricetin | 17 | 75 |
| Quercetin | 82 | 97 |
| Quercitrin | −26 | 23 |
| Rutin | 38 | 55 |

The extract according to the invention was applied in the investigation described above in quantities of 1000 μg. As is evident from Example 1, the extract according to the invention used in accordance with Example 1 (fraction 1) contains 6.3% hyperforin as the active ingredient, with quantitatively the largest portion in the extract. 1000 μg extract thus corresponds to 63 μg hyperforin. The comparison substances were again administered in quantities of 250 μg. This means the test substances were administered at about four times the amount compared with hyperforin. In spite of this, the extract according to the invention shows markedly greater inhibition compared with hyperforin, used as a test substance. Here we see once again the synergistic effect between hyperforin and other ingredients of the extract according to the invention that are relevant for its effectiveness. It thus emerges clearly that the sum-total of the individual compounds is important for its beneficial pharmaceutical properties, where particular flavonoids (e.g. amentoflavone, biapigenine, camphor oil, luteolin, quercetin) are quite plainly of special significance.

EXAMPLE 6

Proliferation of Human Keratinocytes (HaCaT Cells)

The effects of the extracts according to the invention and various ingredients on the proliferation of human keratinocytes were obtained by using the HaCaT cell-line. The cells (10,000–15,000) were disseminated in 200 μl DMEM with 5% foetal calf serum in 96-well F-form micro-titre dishes and incubated at 37° C. at absence of test substances in an incubator. Cell proliferation was determined by measuring the incorporation of $^3H$ methyl-thymidine (0.5 μCi/well) over the last 6 hours in the culture.

| Ingredient | Concentration (μg/ml) | Inhibition (%) |
|---|---|---|
| Extract according to the invention | 30 | 81 |
| Amento-flavone | 10 | 68 |
| Biapigenine | 10 | 15 |
| Catechol | 10 | 14 |
| Chlorogenic acid | 10 | −9 |
| Epicatechol | 10 | 13 |
| Hyperforin Na | 10 | 97 |
| Hypericin | 10 | 100 |
| Hyperoside | 10 | −8 |
| Isoquercitrin | 10 | 83 |
| Camphor oil | 10 | 44 |
| Luteolin | 10 | 92 |
| Myricetin | 10 | 26 |
| Quercetin | 10 | −29 |
| Quercitrin | 10 | 35 |
| Rutine | 10 | 9 |

As is clear from the results set out above, the antiproliferative properties of the extract according to the invention quite plainly have 5 their basis in the combined effect of hypericin and hyperforin, together with certain flavone compounds, for example isoquercitrin and luteolin.

EXAMPLE 7

Inhibition of 5α Reductase

Investigations of 5a reductase inhibition were carried out on cells of the human prostate-cancer cell-line DU145. The cells (250,000) were disseminated in 5 ml of RPMI 1640 medium with 10% foetal calf serum (FCS) in 6-well cell-culture dishes and incubated at 37° C. in an incubator. After four days, the medium against RPMI 1640 was replaced, with the addition of 10% charcoal-stripped FCS. On the following day, the test substances and $^{14}C$ testosterone were applied and another 18 hours later, supernatant of the cells were removed. The supernatant of the cells were mixed with 2.5 ml ethyl acetate and then centrifuged for 10 mins with 500 g at room temperature. The organic phase was removed and transferred over to a small glass tube. Extraction was then repeated by again applying 2.5 ml ethyl acetate. The combined organic phases were evaporated down at 37° C. under $N_2$ fumigation until dry; the residue was taken into 50 μl ethyl acetate and then separated out twice on a silica-gel 60 TLC dish, with ethyl acetate/cyclohexane (1:1) as mobile phase. The testosterone metabolites so formed were localised with the aid of a linear analyser, and inhibition of 5α reductase was obtained at the dihydro-testosterone peak by comparison with the solvent control.

| Ingredient | Concentration (μg/ml) | Inhibition of 5α reductase (%) |
| --- | --- | --- |
| Extract according to the invention in accordance with Example 1 | 500 | 44 |
| Amento flavone | 30 | −15 |
| Biapigenine | 30 | −4 |
| Catechol | 30 | −15 |
| Chlorogenic acid | 30 | 3 |
| Epicatechol | 30 | −6 |
| Hyperforin Na | 5 | 10 |
| Hypericin | 30 | −24 |
| Hyperoside | 30 | −1 |
| Isoquercitrin | 30 | −5 |
| Camphor oil | 30 | 12 |
| Luteolin | 30 | 42 |
| Myricetin | 30 | 29 |
| Quercetin | 30 | 46 |
| Quercitrin | 30 | −29 |
| Rutin | 30 | −6 |

The extract according to the invention shows a marked inhibiting effect on 5a reductase. The concentration of test substances used, at 30 μg/ml, corresponds to the concentration of hyperforin, which is quantitatively the most important ingredient in the extract according to the invention in accordance with Example 1, fraction 1.

In contrast to the extract according to the invention (500 μg/ml), hyperforin turned out to be cyto-toxic at the concentration of some 30 μg/ml corresponding to its proportion of the total extract: hence it was tested only at a concentration of 5 μg/ml. It can be seen from the results that, even at the high concentrations of individual ingredients tested, which clearly exceed their respective proportions in the extract according to the invention, none of these compounds produced an effect exceeding that of the total extract. The overall effect of the extract according to the invention can therefore be explained only by the combined effect of all the ingredients included.

EXAMPLE 8

Stability of the Active Ingredients, in Particular Hyperforin, in the Preparations According to the Invention)

Hyperforin, which is known to be chemically unstable, is included complete in a gel according to the invention in accordance with Example 2a, as can be shown by the quantitative determination of the hyperforin it contains; in other words, no decomposition occurs in producing the gel.

| Preparation | Measured hyperforin concentration (%) | Recovery (%) |
| --- | --- | --- |
| St. John's wort extract according to the invention in accordance with Example 1 | 6.33 | — |
| St. John's wort extract according to the invention in accordance with Example 1/polyacrylate gel | 0.15 | 99.0 |

The invention claimed is:

1. An extract of *Hypericum perforatum L.* having a hyperforin content of 2–8% by weight, a total hypericin content of 0.2–1% by weight and a total flavones content of 2–8% by weight and where the extract is substantially free of chlorophyll and proanthocyanidins.

2. The extract according to claim 1 having a hyperforin content of 4–8% by weight, a total hypericin content of at least 0.4–1% by weight and a total flavone content of 4–8% by weight.

3. The extract according to claim 1 characterised in that the extract in addition contains a stabiliser in an amount of 0.01 to 5% by weight.

4. The extract according to claim 3, characterised in that the stabiliser is selected from the group consisting of ascorbic acid, ascorbic acid esters, organic thiol compounds and complexing agents or mixtures thereof.

5. The extract according to claim 4, wherein the stabilizer is selected from organic thiol compounds and is cysteine or glutathione and the complexing agent is selected from the group consisting of cyclic oligo-saccharides, silicic acids, citric acid, sugar alcohols, cellulose derivatives, polyvinyl-pyrrolidones and vinyl-pyrrolidone-vinylacetate-copolymers, or mixtures thereof.

6. A method for the preparation of an extract of *Hypericum perforatum L.*, comprising extracting dried *Hypericum perforatum L.* plant material with acetone, aqueous acetone, ethanol, aqueous ethanol, or a solvent mixture containing acetone and ethanol to yield a crude extraction mixture, and removing from the crude extraction mixture chlorophyll and proanthocyanidins by filtration using an adsorbing agent.

7. A method according to claim 6, wherein the extracting is done with aqueous acetone or aqueous ethanol, or a mixture of both solvents.

8. A method according to claim 7, wherein ≧90% by weight aqueous acetone or ≧90% by weight aqueous ethanol, or a mixture of both solvents, is deployed for the extracting.

9. A method according to claim 7, wherein the acetone and ethanol solvent mixture has a ratio of 8:2.

10. A method according to any one of claim 6, wherein the adsorbing agent is selected from the group consisting of resins based on polystyrol and argillaceous earth.

11. A method according to claim 6, further comprising adding a stabiliser to the extract.

12. A method according to claim 11, wherein the stabiliser is selected from the group consisting of ascorbic acid, ascorbic acid esters, organic thiol compounds, and complexing agents or mixtures thereof.

13. A method according to claim 12, wherein the stabiliser is selected from organic thiol compounds and is cysteine or glutathione, and the complexing agent is selected from the group consisting of cyclic oligo-saccharides, silicic acids, citric acid, sugar alcohols, cellulose derivatives, polyvinyl-pyrrolidones and vinyl-pyrrolidone-vinylacetate-copolymers, or mixtures thereof.

14. A method according to claim 6, wherein aqueous acetone, aqueous ethanol, or a mixture of both solvents, is used for the extracting; the adsorbing agent is selected from the group consisting of resins based on polystyrol and argillaceous earth; further comprising adding and a stabiliser selected from the group consisting of ascorbic acid, ascorbic-acid esters, organic thiol compounds, and complexing agents or mixtures thereof to the extract.

15. A method according to claim 14, wherein the stabilizer is selected from organic thiol compounds and is cysteine or glutathione, and the complexing agent is selected from the group consisting of cyclic oligo-saccharides, silicic acids, citric acid, sugar alcohols, cellulose derivatives, polyvinyl-pyrrolidones and vinyl-pyrrolidone-vinylacetate-copolymers, or mixtures thereof.

16. A pharmaceutical composition comprising the extract according to claim 1 together with at least one conventional pharmaceutically acceptable excipient for topical application.

17. A pharmaceutical composition according to claim 16 which is formulated as a gel.

18. A method for preparing a pharmaceutical composition according to claim 16, comprising mixing the extract and the at least one conventional pharmaceutically acceptable excipient with a hyperforin stabiliser.

19. A method according to claim 18, wherein the stabiliser is selected from the group consisting of ascorbic acid, ascorbic acid esters, organic thiol compounds and complexing agents or mixtures thereof.

20. A method according to claim 19, wherein the stabilizer is selected from organic thiol compounds and is cysteine or glutathione, and the complexing agent is selected from the group consisting of cyclic oligo-saccharides, silicic acids, citric acid, sugar alcohols, cellulose derivatives, polyvinyl-pyrrolidones and vinyl-pyrrolidone-vinylacetate-copolymers, or mixtures thereof.

21. A method for the treatment of skin and mucous membrane irritations and disorders comprising administering to a patient in need of such treatment a therapeutically effective amount of a the extract according to claim 1.

22. A method according to claim 21, wherein the skin and mucous membrane irritations and disorders are selected from the group consisting of acne, atopic dermatitis, neurodermatitis, psoriasis, stomatitis, herpes zoster, herpes labialis (lip herpes), warts, varicella (chickenpox), sores, burns, and bacterial or viral skin and mucous membrane infections that are accompanied by cell proliferation and inflammation.

23. An extract according to claim 1, having a hyperforin content of 4–8% by weight, a total hypericin content of at least 0.4%–1% by weight and a total flavone content of 4–8% by weight, and comprising a stabiliser in an amount of 0.01 to 5% by weight, wherein the stabiliser is selected from the group consisting of ascorbic acid, ascorbic-acid esters, organic thiol compounds and complexing agents or mixtures thereof.

24. An extract according to claim 23, wherein the stabilizer is selected from organic thiol compounds and is cysteine, and the complexing agent is selected from the group consisting of cyclic oligo-saccharides, silicic acids, citric acid, sugar alcohols, cellulose derivatives, polyvinyl-pyrrolidone and vinyl-pyrrolidone-vinylacetate-copolymers, or mixtures thereof.

* * * * *